United States Patent
Chin

(10) Patent No.: US 9,119,900 B2
(45) Date of Patent: Sep. 1, 2015

(54) UNITARY ENDOSCOPIC VESSEL HARVESTING DEVICES

(71) Applicant: Pavillion Medical Innovations, LLC, Norwell, MA (US)

(72) Inventor: Albert K. Chin, Palo Alto, CA (US)

(73) Assignee: Saphena Medical, Inc., West Bridgewater, MA (US)

( * ) Notice: Subject to any disclaimer, the term of this patent is extended or adjusted under 35 U.S.C. 154(b) by 306 days.

(21) Appl. No.: 13/723,676

(22) Filed: Dec. 21, 2012

(65) Prior Publication Data

US 2013/0165746 A1 Jun. 27, 2013

Related U.S. Application Data

(60) Provisional application No. 61/580,107, filed on Dec. 23, 2011.

(51) Int. Cl.
*A61L 27/36* (2006.01)
*A61B 17/285* (2006.01)
*A61B 18/00* (2006.01)
*A61B 18/04* (2006.01)
(Continued)

(52) U.S. Cl.
CPC ....... *A61L 27/3625* (2013.01); *A61B 17/00008* (2013.01); *A61B 17/285* (2013.01); *A61B 17/320016* (2013.01); *A61B 18/04* (2013.01); *A61B 18/082* (2013.01); *A61B 1/00154* (2013.01); *A61B 2017/00778* (2013.01); *A61B 2017/00969* (2013.01); *A61B 2018/0063* (2013.01); *A61B 2018/00404* (2013.01); *A61B 2018/00595* (2013.01); *A61B 2018/1452* (2013.01)

(58) Field of Classification Search
CPC .......... A61B 17/285; A61B 17/00008; A61B 18/082; A61B 18/04; A61B 2018/145; A61B 2018/1452; A61B 2018/0063; A61B 2018/00601
USPC .................... 606/45–46, 49, 52, 37, 170, 159
See application file for complete search history.

(56) References Cited

U.S. PATENT DOCUMENTS 5,373,840 A 12/1994 Knighton
5,419,767 A * 5/1995 Eggers et al. ................. 604/114
(Continued)

OTHER PUBLICATIONS

International Search Report for International Application No. PCT/US2012/071237 mailed on Feb. 22, 2013.

*Primary Examiner* — Catherine Voorhees
(74) *Attorney, Agent, or Firm* — Greenberg Traurig, LLP; Chinh H. Pham; Roman Fayerberg

(57) ABSTRACT

Unitary surgical devices are disclosed. Such devices may include an elongated body extending between a proximal end and a distal end, and having one or more lumens extending through the elongated body and a tip disposed at the distal end of the elongated body. The harvesting device may further include a first gripping element disposed about the dissection tip and a second gripping element disposed about the dissection tip distally of the first gripping member. The second gripping member may be moveable with respect to the first gripping member for capturing a blood vessel between the first gripping member and the second gripping member. The blood vessel captured between first gripping member and the second gripping member may then be sealed and, subsequently, severed by a cauterizing element disposed between the first gripping member and the second gripping member.

20 Claims, 10 Drawing Sheets

(51) Int. Cl.
*A61B 17/00* (2006.01)
*A61B 17/32* (2006.01)
*A61B 18/08* (2006.01)
*A61B 1/00* (2006.01)
*A61B 18/14* (2006.01)

(56) References Cited

U.S. PATENT DOCUMENTS

| | | |
|---|---|---|
| 5,591,183 A | 1/1997 | Chin |
| 5,695,514 A | 12/1997 | Chin |
| 5,722,576 A | 3/1998 | Rogers |
| 5,797,946 A | 8/1998 | Chin |
| 5,873,889 A | 2/1999 | Chin |
| 5,891,141 A | 4/1999 | Rydell |
| 5,895,353 A | 4/1999 | Lunsford et al. |
| 5,916,233 A | 6/1999 | Chin |
| 5,921,919 A | 7/1999 | Chin et al. |
| 5,968,065 A | 10/1999 | Chin |
| 5,976,168 A | 11/1999 | Chin |
| 5,980,549 A | 11/1999 | Chin |
| 5,984,937 A | 11/1999 | Morse et al. |
| 6,036,714 A | 3/2000 | Chin |
| 6,053,863 A | 4/2000 | Chin et al. |
| 6,071,232 A | 6/2000 | Knighton et al. |
| 6,162,173 A | 12/2000 | Chin et al. |
| 6,176,825 B1 | 1/2001 | Chin et al. |
| 6,203,557 B1 | 3/2001 | Chin |
| 6,264,670 B1 | 7/2001 | Chin |
| 6,277,137 B1 | 8/2001 | Chin |
| 6,348,037 B1 | 2/2002 | Chin et al. |
| 6,406,425 B1 | 6/2002 | Chin et al. |
| 6,428,468 B1 | 8/2002 | Knighton et al. |
| 6,428,556 B1 | 8/2002 | Chin |
| 6,432,044 B1 | 8/2002 | Lunsford et al. |
| 6,506,200 B1 | 1/2003 | Chin |
| 6,511,494 B1 | 1/2003 | Knighton et al. |
| 6,558,313 B1 | 5/2003 | Knighton et al. |
| 6,607,547 B1 | 8/2003 | Chin |
| 6,660,016 B2 | 12/2003 | Lindsay |
| 6,705,986 B2 | 3/2004 | Fiegel |
| 6,706,052 B1 | 3/2004 | Chin |
| 6,752,756 B2 | 6/2004 | Lunsford et al. |
| 6,811,546 B1 | 11/2004 | Callas et al. |
| 6,830,546 B1 | 12/2004 | Chin et al. |
| 6,951,568 B1 | 10/2005 | Chin |
| 6,976,957 B1 | 12/2005 | Chin et al. |
| 7,001,404 B1 | 2/2006 | Chin |
| 7,041,113 B2 | 5/2006 | Gruhl et al. |
| 7,066,875 B2 | 6/2006 | Knighton |
| 7,077,803 B2 | 7/2006 | Kasahara et al. |
| 7,326,178 B1 | 2/2008 | Lunsford et al. |
| 7,331,971 B2 | 2/2008 | Kasahara et al. |
| 7,384,423 B1 | 6/2008 | Chin |
| 7,476,198 B1 | 1/2009 | Chin et al. |
| 7,510,562 B2 * | 3/2009 | Lindsay .................. 606/159 |
| 7,534,243 B1 * | 5/2009 | Chin et al. .............. 606/49 |
| 7,544,195 B2 | 6/2009 | Lunsford et al. |
| 7,547,314 B2 | 6/2009 | Kadykowski |
| 7,556,633 B2 | 7/2009 | Lindsay |
| 7,662,153 B2 | 2/2010 | Gruhl et al. |
| 7,695,470 B1 | 4/2010 | Stewart |
| 7,867,163 B2 | 1/2011 | Chin et al. |
| 7,887,558 B2 | 2/2011 | Lin et al. |
| 7,918,848 B2 | 4/2011 | Lau et al. |
| 7,959,553 B2 | 6/2011 | Knighton et al. |
| 7,981,127 B2 | 7/2011 | Kasahara et al. |
| 7,981,133 B2 | 7/2011 | Chin |
| 8,048,100 B2 | 11/2011 | Kadykowski et al. |
| 8,075,559 B2 | 12/2011 | Stewart et al. |
| 8,097,010 B2 | 1/2012 | Kasahara et al. |
| 8,197,472 B2 | 6/2012 | Lau et al. |
| 8,337,412 B2 | 12/2012 | Fuller et al. |
| 2002/0183593 A1 | 12/2002 | Chin et al. |
| 2003/0032861 A1 | 2/2003 | Lunsford et al. |
| 2003/0130674 A1 | 7/2003 | Kasahara et al. |
| 2005/0149094 A1 | 7/2005 | Kasahara et al. |
| 2005/0154257 A1 | 7/2005 | Kasahara et al. |
| 2005/0159764 A1 | 7/2005 | Kasahara et al. |
| 2005/0192613 A1 | 9/2005 | Lindsay |
| 2006/0173453 A1 | 8/2006 | Gruhl et al. |
| 2006/0211916 A1 | 9/2006 | Kasahara et al. |
| 2006/0217697 A1 | 9/2006 | Lau et al. |
| 2006/0217706 A1 | 9/2006 | Lau et al. |
| 2006/0287574 A1 | 12/2006 | Chin |
| 2007/0149993 A1 | 6/2007 | Kasahara et al. |
| 2008/0103365 A1 | 5/2008 | Lunsford et al. |
| 2008/0132892 A1 | 6/2008 | Lunsford et al. |
| 2008/0208191 A1 | 8/2008 | Kadykowski et al. |
| 2008/0208192 A1 | 8/2008 | Kadykowski et al. |
| 2008/0306335 A1 | 12/2008 | Lau et al. |
| 2009/0023986 A1 | 1/2009 | Stewart et al. |
| 2009/0024156 A1 | 1/2009 | Chin |
| 2009/0139531 A1 | 6/2009 | Fuller et al. |
| 2009/0299367 A1 | 12/2009 | Ginnebaugh et al. |
| 2009/0306699 A1 | 12/2009 | Kadykowski et al. |
| 2010/0042099 A1 | 2/2010 | Lunsford et al. |
| 2010/0191043 A1 | 7/2010 | Chin |
| 2010/0234843 A1 | 9/2010 | Stewart et al. |
| 2010/0292532 A1 | 11/2010 | Kadykowski et al. |
| 2010/0292533 A1 | 11/2010 | Kasahara et al. |
| 2011/0046624 A1 | 2/2011 | Lin |
| 2011/0202082 A1 | 8/2011 | Chin |
| 2011/0257643 A1 | 10/2011 | Lau et al. |
| 2011/0288369 A1 | 11/2011 | Ginnebaugh et al. |
| 2011/0288546 A1 | 11/2011 | Abbott et al. |
| 2012/0046677 A1 | 2/2012 | Lin et al. |
| 2012/0078037 A1 | 3/2012 | Stewart et al. |
| 2012/0316550 A1 | 12/2012 | Lau et al. |
| 2013/0197299 A1 * | 8/2013 | Chin et al. .............. 600/36 |

* cited by examiner

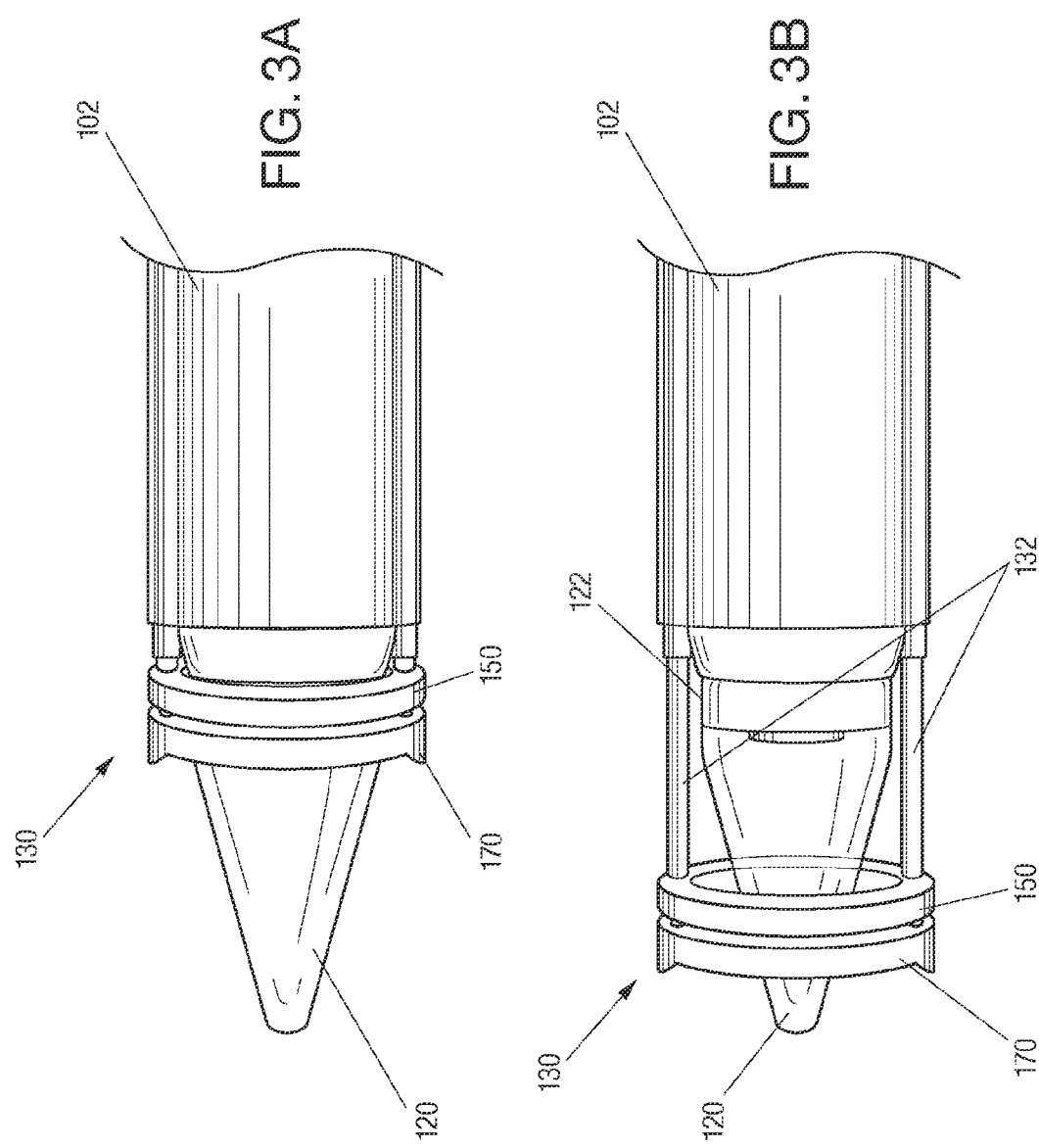

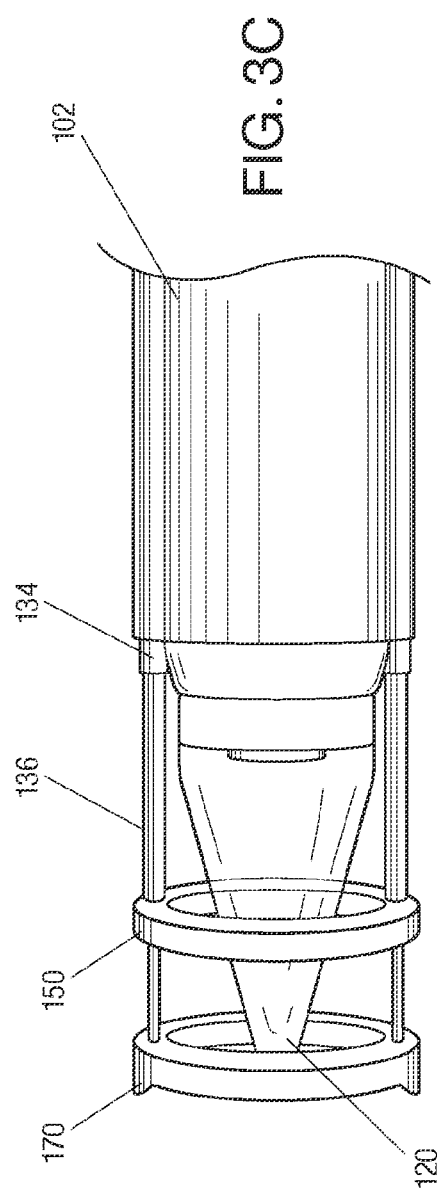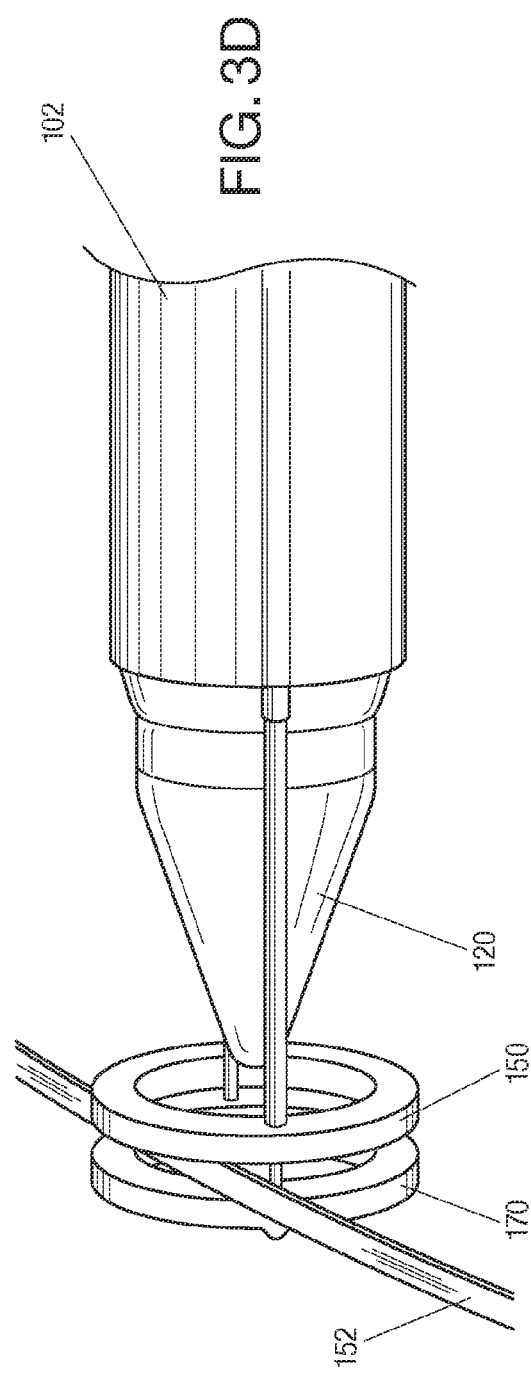

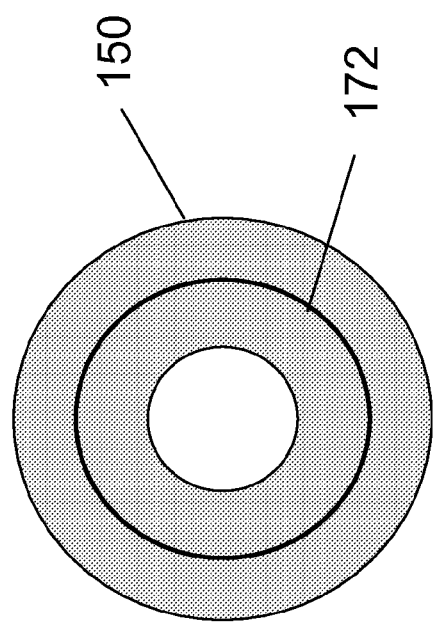
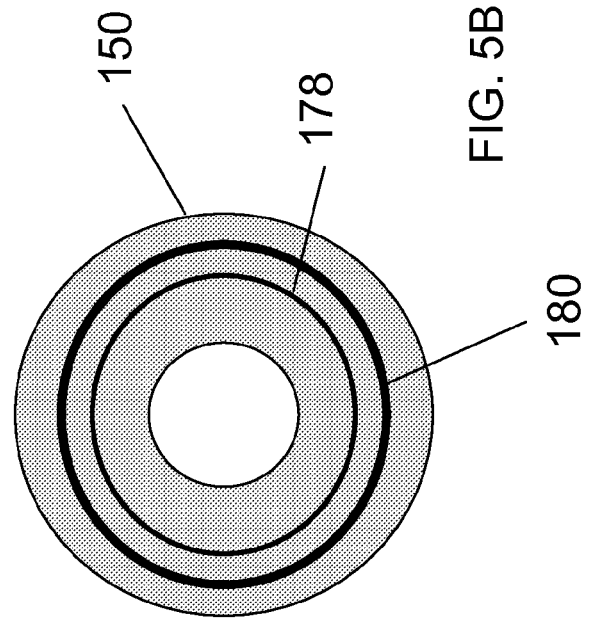

UNITARY ENDOSCOPIC VESSEL HARVESTING DEVICES

RELATED APPLICATION

This application claims priority to and benefit of U.S. Provisional Application No. 61/580,107, filed Dec. 23, 2011, which application is hereby incorporated herein by reference in its entirety.

TECHNICAL FIELD

The presently disclosed embodiments relate to endoscopic cannulas and methods of their use.

BACKGROUND

Vessel harvesting is a surgical technique that is commonly used in conjunction with coronary artery bypass surgery. During a bypass surgery, blood is rerouted to bypass blocked arteries to restore and improve blood flow and oxygen to the heart. The blood may be rerouted using a bypass graft, where one end of the by-pass graft is attached to a blood source upstream of the blocked area and the other end is attached downstream of the blocked area, creating a "conduit" channel or new blood flow connection bypassing the blocked area. Commonly, a surgeon will remove or "harvest" healthy blood vessels from another part of the body to create the bypass graft. The success of coronary artery bypass graft surgery may be influenced by the quality of the conduit and how it is handled or treated during the vessel harvest and preparation steps prior to grafting.

Vessel harvesting methods involve selecting a vessel, traditionally, the great saphenous vein in the leg or the radial artery in the arm to be used as a bypass conduit sealing off and cutting smaller blood vessels that branch off the main vessel conduit and harvesting the main conduit from the body. This practice does not harm the remaining blood vessel network, which heals and maintains sufficient blood flow to the extremities, allowing the patient to return to normal function without noticeable effects.

Minimally invasive technique for vessel harvesting is known as endoscopic vessel harvesting, a procedure that requires only small incisions. While the endoscopic vessel harvesting procedure is an improvement over a traditional "open" procedure that required a single, long incision from groin to ankle, the endoscopic procedure is still cumbersome and difficult. In particular, current endoscopic harvesting systems require multiple tools, which increases the potential for injury to the bypass conduit as well as increases the duration of the procedure. Accordingly, improvements in systems and methods for endoscopic vessel harvesting are still needed.

SUMMARY

Unitary endoscopic vessel harvesting device are disclosed. In some aspects, there is disclosed a surgical device for harvesting a blood vessel that may include an elongated body extending between a proximal end and a distal end, and having one or more lumens extending through the elongated body and a tip disposed at the distal end of the elongated body. The harvesting device may further include a first gripping element disposed about the dissection tip and a second gripping element disposed about the dissection tip distally of the first gripping member. The second gripping member may be moveable with respect to the first gripping member between an open position away from the first gripping member to a closed position toward the first gripping member for grasping a blood vessel between the first gripping member and the second gripping member. The blood vessel grasped between first gripping member and the second gripping member may be sealed and severed by a cauterizing element disposed between the first gripping member and the second gripping member such that the blood vessel gripped between the first gripping member and the second gripping member is pressed against the cauterizing element for sealing. Once the blood vessel is sealed, the cauterizing element may also be used to sever the blood vessel.

In some aspects, there is disclosed a device for harvesting a blood vessel that may include an elongated body an elongated body extending between a proximal end and a distal end, and having one or more lumens extending through the elongated body. A deflectable tip may be disposed at the distal end of the elongated body. The vessel harvesting device may further include a gripping unit disposed about the dissection tip, the gripping unit including a proximal member and a distal member configured to capture a blood vessel therebetween The vessel harvesting device may also include a cauterizing element supported by the gripping unit such that the blood vessel captured by the gripping unit is pressed against the cauterizing element to allow the cauterizing element to seal for subsequent severing of the blood vessel.

In some aspects, there is disclosed a method for harvesting a blood vessel. First, a dissection tip disposed at a distal tip of an elongated body may be advanced along a main vessel to dissect the blood vessel and its branch vessels from the surrounding tissue. Upon encountering a branch vessel, a gripping unit may be activated to capture the branch vessel between a proximal member and a distal member of the gripping unit. Capturing the branch vessel between the proximal member and the distal member of the gripping unit may press the captured branch vessel against a cauterizing element supported by the gripping unit. Next, the cauterizing unit may be activated to seal and sever the captured branch vessel. This process may be repeated until a section of the main vessel of a desired length has been dissected and the branch vessels along this section have been severed. The main vessel may then be captured between the proximal member and the distal member and pressed against the cauterizing element supported by the gripping unit. The cauterizing element may again be energized to first seal and then sever the blood vessel.

BRIEF DESCRIPTION OF DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 3A-3D are close ups of the distal region of an endoscopic cannula of the present disclosure.

FIGS. 5A-5B illustrate embodiments of a cauterizing element of an endoscopic cannula of the present disclosure for severing and sealing a blood vessel.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides a unitary device for endoscopic vessel harvesting. Present systems for endoscopic vessel harvesting contain multiple components. Typically, an endoscopic dissection device is used to isolate the main vessel from the surrounding connective tissue by dissecting the main vessel from surrounding connective tissue. An endoscopic cannula is then used to introduce an endoscopic tributary sealing instrument to seal side branches. Once the side branches are sealed, yet another device is used to harvest a section of the main vessel to be used as a bypass graft. The unitary devices of the present disclosure combine the dissection function, the tributary sealing and severing function, and, optionally, main vessel sealing and severing function, which can result in decreased vessel manipulation and improvement in ease of the procedure. The devices of the present disclosure may also be used to extract the sealed and severed main vessel from the patient.

Decreased vessel manipulation may decrease the potential for injury to the graft. Repeated vessel contact with multiple passes of harvesting instrumentation increases potential vessel injury. A unitary device such as the device of the present disclosure may dissect, i.e., separate the main vessel, from surrounding tissue, cauterize and transect the tributaries and the main vessel as the device is advanced, and the vessel may be harvested with a single passage of the device, rather than multiple device insertions and retractions. Such a device with a decreased diameter may be used for dissection as well as tributary ligation; graft trauma should be decreased. The relative smaller diameter of the present device can also facilitate harvesting of more tortuous vessels; for example, the internal mammary artery.

Figure 1:
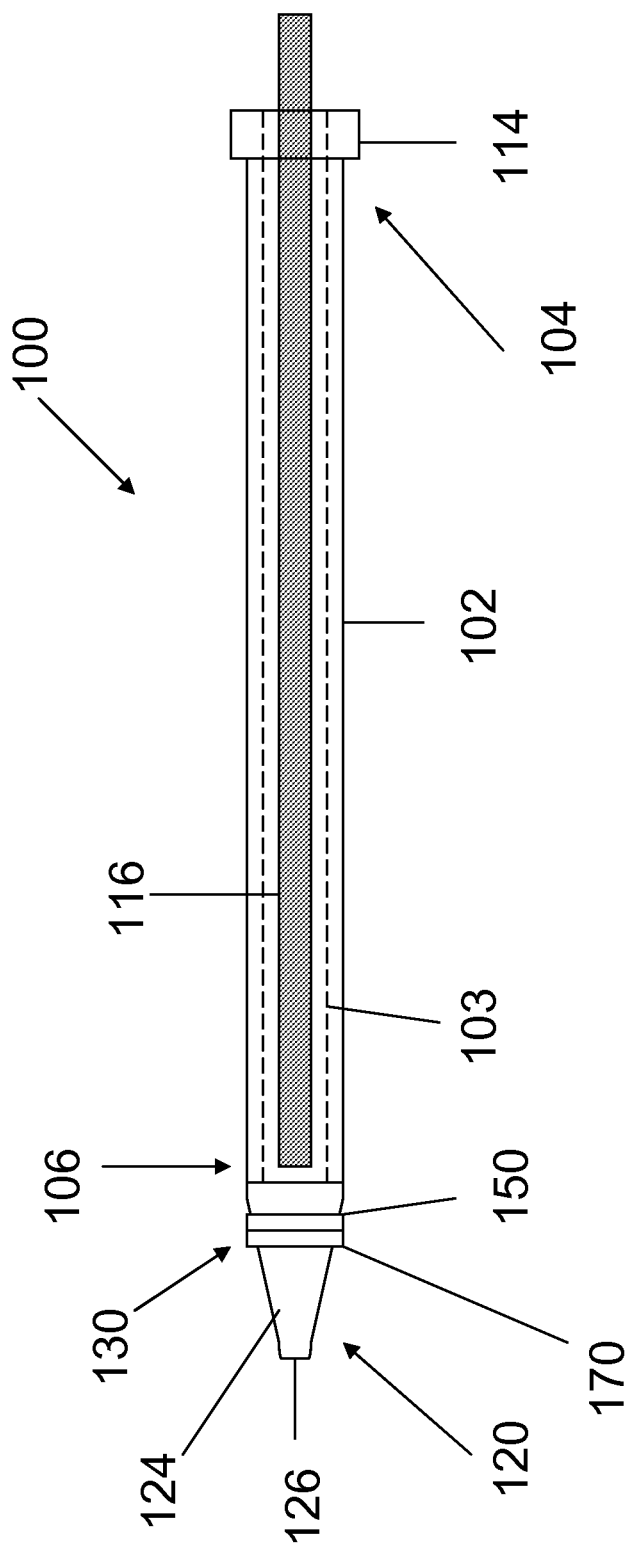
FIG. 1 illustrates a side view of an endoscopic cannula of the present disclosure.

Referring to FIG. 1, an endoscopic cannula 100 of the present disclosure includes an elongated body 102 having a proximal end 104 and a distal end 106. In some embodiments, the elongated body 102 is configured for passing extravascularly through an entry incision to a vessel harvesting site. To aid in navigating the elongated body 102 to a site of harvesting, the elongated body 102 may be sufficiently rigid axially along its length. To provide the elongated body 102 with such characteristic, in an embodiment, the elongated body 102 may be made from a plastic material, metallic material, shape memory material, composite material or any other materials that has the desired characteristics. To the extent desired, the elongated body 102 may be provided with some flexibility to move radially or laterally from side to side depending on the application.

The endoscopic cannula 100 may be a multi-lumen cannula with lumena that accommodate advancing instruments or materials therethrough. The endoscopic cannula 100 may include an endoscopic lumen 103 into which an endoscope 116 may be inserted for visualizing procedures performed using the cannula 100. The endoscopic cannula 100 may include an adapter 114 at the proximal end 104 for advancing the endoscope 116 into the endoscopic cannula 100. Additional lumens of the cannula 100 are described below.

In some embodiments, the endoscopic cannula 100 may include a dissection tip 120 disposed at or about the distal end 106 of the endoscopic cannula 100. The dissection tip 120 may include an inner cavity in fluid communication with the endoscopic lumen 103 to enable the endoscope 116 to be advanced into the dissection tip 120. The tip 120 may be transparent to allow for endoscopic viewing through the tip 120 of the procedures performed using the cannula 100. The dissection tip 120 may be provided with any shape as long as it facilitates endoscopic viewing therethrough, and allows for necessary control during tissue dissecting, i.e. separation. In some embodiments, the dissection tip may be generally conical. In some embodiments, the dissection tip 120 may include a generally flat shoulder 122 (best seen in FIG. 3B), and a tapered section 124 which terminates in blunt end 126 for atraumatic separation of a vessel segment, being harvested from surrounding tissue, while preventing tearing or puncturing of nearby vessels or tissue as the endoscopic cannula 100 is navigated along the vessel segment. It should of course be understood that, to the extent desired, the end 126 of the dissection tip 120 may be made substantially sharp.

To further reduce likelihood of trauma during the dissection process, in some embodiments, the dissection tip 120 may be radially pliable, flexible or deformable so that the dissection tip may deflect slightly under exertion of force applied to the dissection tip 120, such as when a side branch is encountered during the dissection. In some embodiments, the dissection tip 120 is radially compressible so that the walls of the dissection tip 120 can deform under exertion of force normal to the tip surface. To that end, the dissection tip 120 may be formed from thin wall plastic material, such as polycarbonate or polyethylene terephthalate glycol-modified (PETG), to enable the dissection tip to flex under load. At the same time, the dissection tip 120 may be provided with sufficient column strength in axial or longitudinal direction to allow dissection of the vessel from the surrounding connective tissue.

Figure 2A:
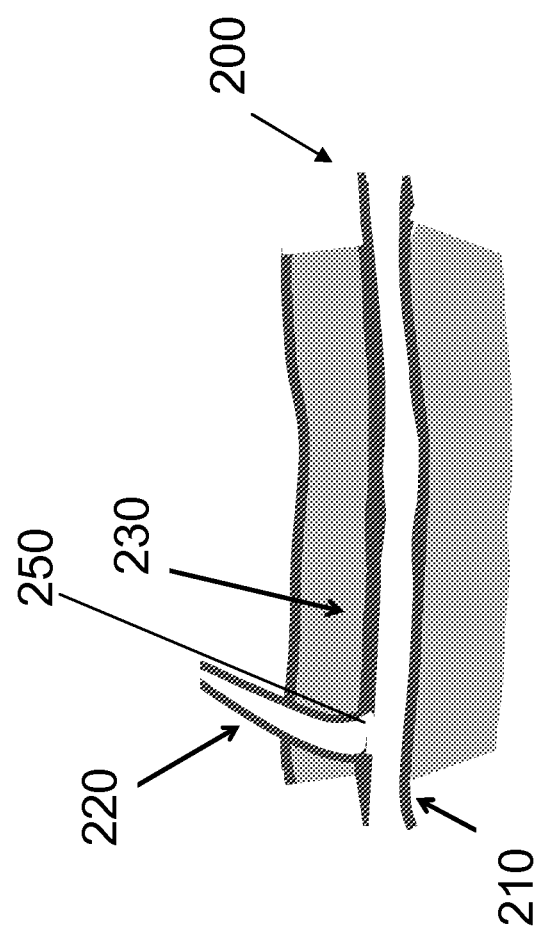
FIGS. 2A-FIG. 2C illustrate a dissection procedure using an endoscopic cannula of the present disclosure.
Figure 2B:
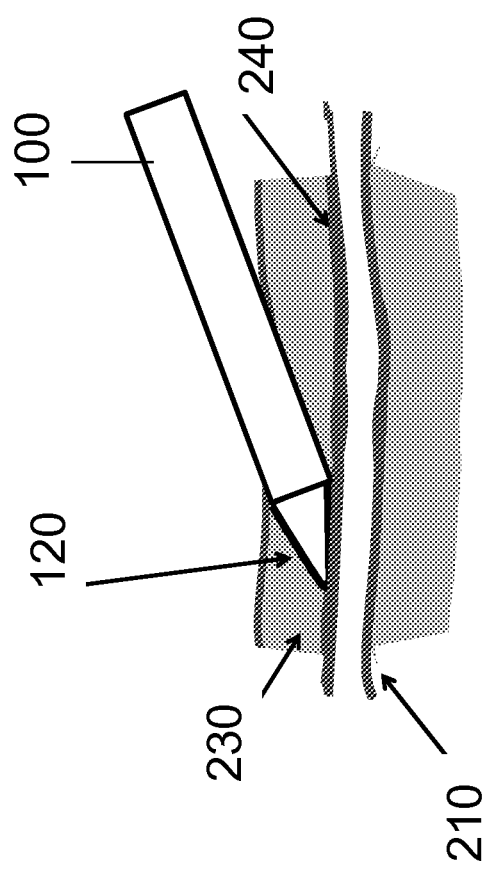
Figure 2C:
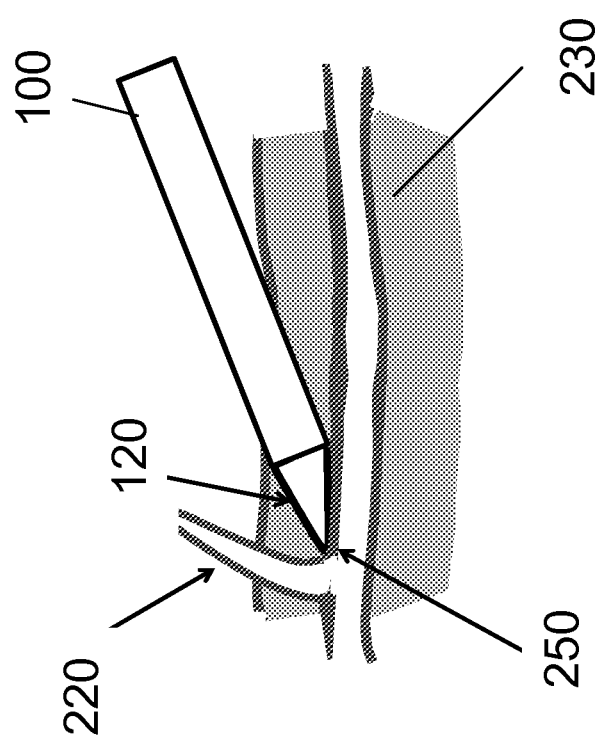

In reference to FIGS. 2A-2C, blood vessels used in bypass grafting (e.g. greater saphenous vein or radial artery), lie in the subcutaneous space, beneath the surface of the skin. The vessel 200 is composed of a main trunk 210, and branch vessels 220 that emanate from the vessel trunk 210, as shown in FIG. 2A. The vessel 200 and its branches 210 are encased in subcutaneous fatty connective tissue 230, and need to be dissected free of the surrounding fatty connective tissue 230 before the main vessel 200 may be harvested. The subcutaneous fat 230 is softer than skin, muscle, fascia or other connective tissues. Although adherent to the vessel 200, the fatty connective tissue 230 forms an interface 240 with the vessel 200 that may be cleanly dissected; that is, there is a natural dissection plane between the outer layer of the vessel 200 (the adventitia), and the surrounding subcutaneous fat 230.

FIG. 2B illustrates dissection of the main trunk 210 of the vessel 200 with the dissection tip 120 along the natural dissection plane, with the dissection tip 120 advanced along the adventitial surface of the vessel 200. Isolation of the vessel 200 from surrounding fatty connective tissue 230 along this plane, typically, does not require high dissection forces. In some embodiments, the dissection tip may 120 be provided with sufficient column strength to dissect the vessel 200 from the surrounding tissue 230 along the natural dissection plane between them.

On the other hand, as is illustrated in FIG. 2C, as the dissection tip 120 approaches a branch vessel 220, the dissection tip 120 may catch the branch vessel 220 at a junction 250 between the branch vessel 220 and the main vessel 200.

Application of excessive force with the dissection tip 220 may avulse the branch vessel and sever it from the trunk vessel, or may otherwise cause damage to the main vessel 200. To that end, in some embodiments, the dissection tip 120 is provided with sufficient column strength to dissect the vessel 200 from the surrounding tissue 230 along the natural dissection plane between them, while being sufficiently pliable to deform or deflect from the branch vessel 220 with the application of increased force, to decrease the potential of trauma to the graft vessel during dissection around branch vessels. It should of course be understood that the rigidity of the dissection tip 120 may be varied from fully flexible to semi-rigid to rigid, in accordance with requirements of the procedure.

Referring back to FIG. 1, the endoscopic cannula 100 may further include a gripping unit 130 situated about the dissection tip 120 for sealing and cutting a blood vessel, either a branch vessel or the main vessel. In some embodiments, the gripping unit 130 may comprise a proximal member 150 and a distal member 170 configured to grasp a vessel between them so that the vessel may be sealed and subsequently cut.

In reference to FIG. 3A and FIG. 3B, in some embodiments, the gripping unit 130 may be translateable relative to the dissection tip 120 from a proximal position to a more distal position. For example, FIG. 3A illustrates the gripping unit 130 at a proximal position at the proximal shoulder of the dissection tip 120. The gripping unit 130 may be positioned at such proximal position during the advancement of the cannula 100 to a site of vessel harvesting or during dissection. The gripping unit 130 may be configured to be substantially flush with the outer surface of the elongated body 102 of the cannula 100 when at the proximal position to minimize obstruction during the advancement of the cannula 100 to a site of vessel harvesting and during dissection. On the other hand, as illustrated in FIG. 3B, the gripping unit 130 may be translated to a more distal position for sealing or severing of a vessel. In some embodiments, the gripping unit 130 may be advanced distally past the dissection tip 120.

To permit translation of the gripping unit 130 relative to the dissection tip 120, in some embodiments, the gripping unit 130 may be mounted on one or more actuating rods 132 for advancing and retracting the gripping unit 130 relative to the dissection tip 120. The actuating rods 132 may be passed from the gripping unit 130 proximally through a one or more lumens of the elongated body 102 of the cannula 100 to allow the user to control the translation of the gripping unit 130 from the proximal end 104 of the cannula 100. It should, of course, be understood that other mechanisms for translating the gripping unit 130 relative to the dissection tip 120 may be employed.

As shown in FIG. 3B, in some embodiments, the proximal member 150 and the distal member 170 may be translated relative to the dissection tip together as a unit. In this manner, the visualization of vessel cutting may be enhanced, as both the proximal member 150 and the distal member 170 may be moved forward so that they may be visible the endoscopic view.

Moreover, as shown in FIG. 3C, the proximal member 150 and the distal member 170 may be separated from one another to permit positioning a vessel 152 to be sealed and cut between the proximal member 150 and the distal member 170. The proximal member and the distal member may then be compressed against one another to capture the vessel therebetween, as shown in FIG. 3D. While FIG. 3D illustrates the proximal member and the distal member translated past the dissection tip 120, the proximal member 150 and the distal member 170 are designed to be able to capture a vessel in a position over the dissection tip 120, which may also assist the members 150, 170 in securely holding the vessel. In order to achieve movement of the proximal member 150 relative to the distal member 170, the actuating rods 132 may include one or more two tubular rods 134 for supporting one member of the gripping unit 130, while one or more smaller rods 136 may be slidably disposed inside the tubular rods for supporting the other member of the gripping unit 130, thus enabling the relative movement of the proximal member 150 and the distal end 170. It should of course be understood that, in some embodiments, only the distal member 170 may be translatable relative to the dissection tip 120 and the proximal member 150 may be stationary positioned at the proximal position relative to the dissection tip 120 or another desired position.

Figure 4:
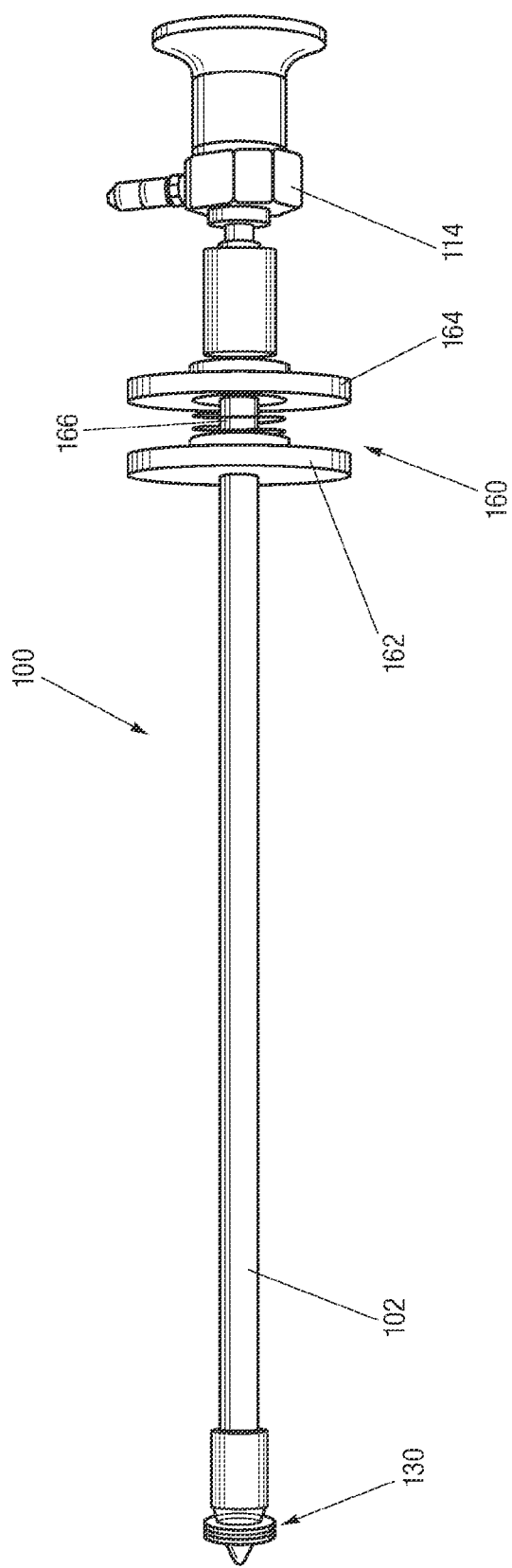
FIGS. 4A-4E illustrates a perspective view of an endoscopic cannula of the present disclosure with a spring loaded gripping unit.

In reference to FIGS. 4A-4E, in some embodiments, the proximal member 150 and the distal member 170 may be biased towards one another to securely grip a vessel in-between the proximal member 150 and the distal member 170. In some embodiments, the distal member 170 may be spring loaded with respect to the proximal member 150, using, for example, a proximal actuating system 160 operationally connected to the proximal member 150 and the distal member 170 of the gripping unit 130, as shown in FIG. 4A. This may allow the distal member 170 and the proximal member 150 to securely clip onto the vessel to be sealed and cut, and to stabilize the vessel in preparation for and during sealing and cutting the vessel. The spring force of the spring loaded version may determine the amount of compression applied to the vessel between the proximal member 150 and the distal member 170. Thus, in some embodiments, the spring is selected to provide sufficient strength for the gripping unit 130 to securely grip and hold a vessel, without damaging the vessel.

By way of a non-limiting example, the actuating system 160 may comprise two controlling members 162, 164 disposed on the actuating rods 132 and biased away to one another with the spring 166. One controlling member is connected to the proximal member 150 via an actuating rod and the second controlling member is connected to the distal member 170 via an actuating rod, such that the movement of controlling members 162, 164 translates the proximal member 150 and the distal member 170. Accordingly, the position of the proximal member 150 and the distal member 170 with respect to the dissection tip 120 and one another may be controlled by the user by adjusting the position of the controlling member 162, 164.

Figure 4C:
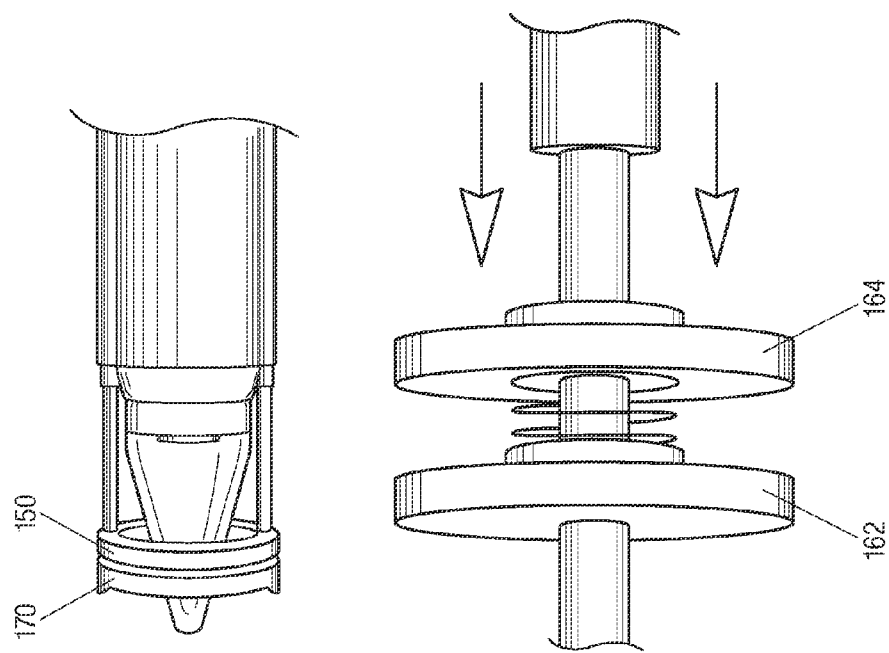
Figure 4B:
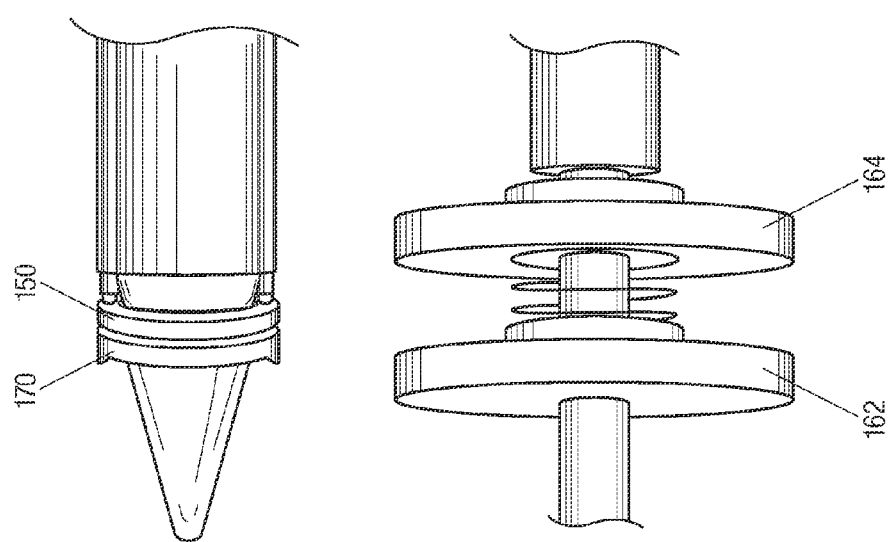
Figure 4D:
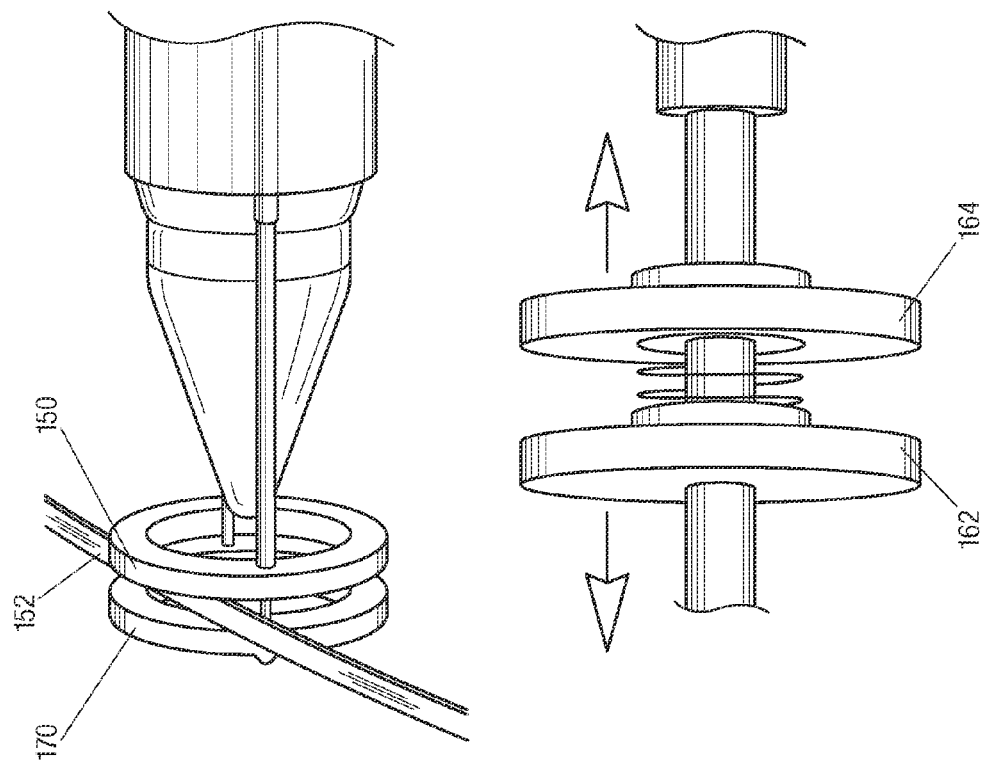
Figure 4E:
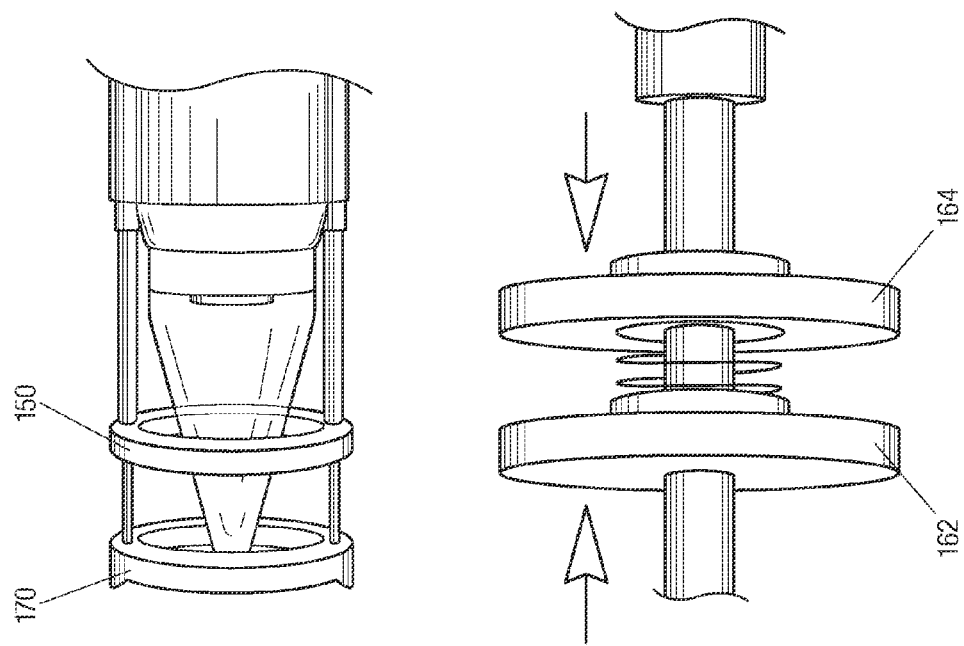

FIG. 4B illustrates the proximal member 150 and the distal member 170 together at the proximal position. Next, as shown in FIG. 4C, the proximal member 150 and the distal member may be translated in the distal direction relative to the dissection tip 120 by distally advancing the controlling member 162, 164 of the proximal actuation system 160. As shown in FIG. 4D, when the proximal member 150 and the distal member 170 are placed near a vessel 152 that needs to be severed, the proximal member 150 and the distal member 170 may be pried apart by pushing the controlling member 162, 164 toward one another so that the vessel 152 may be positioned in the space between the proximal member 150 and the distal member 170. Finally, as shown in FIG. 4E, the controlling member 162, 164 may be allowed to return to their original position (spaced away from one another) due to the spring force of the spring 166 to cause the proximal member 150 and the distal member 170 to compress against one another to securely capture the vessel between the proximal member 150 and the distal member 170, and hold the vessel 152 steady during the cutting and sealing step. In some embodiments, a lever or other mechanical actuator may move and bias the distal member 170 and the proximal member 150 with respect to one another. A force limiting mechanism may be incorporated into the actuator, to control the compressive force exerted on the vessel when the distal member 170 and the proximal member 150 are pressed together.

In some embodiments, the proximal member 150 and the distal member 170 may be toroidal or circular in shape. The circular configuration of the gripping unit 130 may facilitate capture of a vessel regardless of the position and orientation of the cannula 100 relative to the vessel. In some embodiments, the diameter of the circular proximal member 150 and the distal member 170 may be selected depending on the size of the vessel that will need to be captured between the proximal member 150 and the distal member 170, thus providing flexibility to the cannula to be used to sever and seal branch vessels as well as the main trunk. The shape of the dissection tip 120, how far distally the gripping unit 130 may be translated, or both may also be adjusted to allow the gripping unit 130 to accommodate vessels of varying size. In general, the larger the clearance from the surface of the dissection tip 120 to the top of the gripping unit 130, the larger the vessel that can be accommodated between the proximal member 150 and the distal member 170 without causing the vessel to slip out from the gripping unit 130. In some embodiments, by allowing the gripping unit 130 to translate past the distal tip of the dissection tip 120, larger vessels may be accommodated in the gripping unit 130. In some embodiments, the ring-shaped proximal member 150 and the distal member 170 may be concentrically positioned about the dissection tip 120. It should be noted that the proximal member 150 and the distal member 170 may be provided with a different shape as long as the gripping unit 130 is capable of sealing and severing a blood vessel.

Referring to FIG. 5A, the endoscopic cannula 100 may include a cauterizing element 172 disclosed on the gripping unit 130, the cauterizing element being configured to cauterize or seal a blood vessel. Once the blood vessel is sealed, the cauterizing element may then be used to sever or transect the blood vessel. The cauterizing element 172 may be positioned along an inside face of the proximal member 150 such that when the proximal member 150 and the distal member 170 are closed together, a blood vessel positioned between the proximal member 150 and the distal member 170 may be compressed in close proximity to, or in direct contact, with the cauterizing element 172 to enable the cauterizing element 172 to seal and sever the vessel. It should of course be understood that the cauterizing element may be positioned along an inner face of the distal member 170, or each the proximal member 150 and the distal member 170 may be provided with cauterizing elements designed to cooperate to seal and sever of the vessel positioned between the proximal member 150 and the distal member 170. To the extent desired, the proximal member 150 and the distal member 170 may be configured to assist the cauterizing element 172 in sealing and severing the vessel. By way of a non-limiting example, the inner surfaces of the proximal member 150 and the distal member 170 may be provided with cooperating sharp edges to sever the vessel.

In some embodiments, the cauterizing element 172 may be made of a wire that can be connected to an electricity source by an electrode extending proximally from the cauterizing element 172 through a lumen of the cannula 100. In some embodiments, the one or more supporting rods may act to conduct electricity from the electricity source to the wire 172. The wire can be heated to a desired temperature by conducting electrical current supplied by an electricity source to permit the cauterizing element to seal and sever the vessel compressed against it by the cooperating proximal member 150 and distal member 170.

In reference to FIG. 5B, in some embodiments, the cauterizing element 172 may comprise a transecting or severing wire 178 and a sealing or cauterizing wire 180. Both wires may be connected to a source of electricity with an electrode. The transecting (inner wire) 178 may have a smaller cross-sectional diameter than the sealing wire with a higher electrical resistance resulting in a higher wire temperature for vessel transection. Instead, due to lower resistance the sealing wire 180 may achieve a lower temperature for vessel sealing. This allows the vessel to be sealed proximal to the transection site. It should be noted that, in some embodiments, the transecting wire 178 and the sealing wire 180 may be disposed on different members of the gripping unit 130. In some embodiments, instead of two wires, a continuous spiral wire of variable diameter may be utilized, with the inner portion of the spiral wire having a smaller wire diameter than the outer portion of the spiral wire, which may eliminate a need for multiple electrodes.

In some embodiments, the cauterizing element 172 may be connected to a battery for supplying electrical current to the cauterizing element 172 to heat the cauterizing element 172. Manually controllable switch or a timer for controlling the heating of the cauterizing element 172 may be provided on the endoscopic cannula 100 at a location that is conveniently operable by the user's thumb or finger. Of course, electrical current can also be supplied from an external source through, for example, a foot-operated controller to selectively heat the cauterizing element 172. In other embodiments, instead of electrical current, a relatively high level of radiant energy may be supplied along a fiber optical channel, for example, from an external laser to an absorptive load that is thereby heated to cut and seal the vessel. In yet other embodiments, an ultrasonic crystal resonator or other vibrator may be utilized to ultrasonically heat the vessel compressed inside the gripping unit 130 in response to ultrasonic signal applied to the vessel. Radiofrequency energy may also be transmitted through wires 178 and 180. Monopolar radiofrequency current may be transmitted through each wire separately. Conversely, bipolar electrocautery current may be applied between wires 78 and 180 to cauterize tissue incorporated between the outer wire 180 and the inner wire 178.

In operation, an initial incision may be made in conventional manner to expose the target vessel (e.g., the saphenous vein). The cannula 100 may be inserted into the incision and guided to the target vessel. The cannula 100 may then be advanced substantially along the target vessel to dissect the target vessel from the surrounding tissue. In some embodiments, the cannula 100 may be introduced through a sealable port used to seal the incision to allow insufflation of the space created by the dissection of the target vessel from surrounding tissues.

As the cannula 100 is being advanced, the proximal member 150 and the distal member 170 of the gripping unit 130 may be kept in the proximal position to reduce the profile of the cannula 100 and to provide a substantially unobstructed view of the dissection procedure. As a branch vessel is encountered along the target vessel, connective tissue around the branch vessel may be dissected away from and around the branch vessel. Once the branch vessel has been dissected from the surrounding tissue, the gripping unit 130 may be activated to capture the branch vessel between the proximal member 150 and the distal member 170 of the gripping unit 130 and the cauterizing element 172 may be activated to seal and sever the branch vessel. The distance from the target vessel at which the branch vessel is severed may be controlled by lateral displacement of the gripping unit 130 relative to the dissection tip 120.

After the branch vessel has been hemostatically severed, the gripping unit 130 may be returned to the proximal position and the cannula 100 may be advanced forward until the next branch vessel is encountered, at which point the branch vessel may sealed and severed using the gripping unit 130. Once all branch vessels along a desired length of the target vessel have been sealed and severed, the cannula 100 may be used to seal and cut the target vessel according to procedure similar to the procedure used to cut and seal the branch vessel, except that the gripping unit 130 may have to be advanced further along the dissection tip 120, or even past the dissection tip 120, to be able to accommodate the larger target tissue between the proximal member 150 and the distal member 170. The target vessel may then be extracted through the incision for use as a by-pass graft.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. An surgical device comprising:
   an elongated body extending between a proximal end and a distal end, and having one or more lumens extending through the elongated body;
   a tip disposed at the distal end of the elongated body;
   a first gripping member having a ring shape and being positioned concentrically around the tip;
   a second gripping member having a ring shape and being positioned concentrically around the tip distally of the first gripping member, the first and second gripping members being independently moveable along a longitudinal direction of the tip with respect to one another between an open position where the second gripping member is spaced away from the first gripping member and a closed position where the second gripping member is next to the first gripping member for gripping a blood vessel between the first gripping member and the second gripping member; and
   a cauterizing element disposed between the first gripping member and the second gripping member so that the blood vessel, when gripped between the first gripping member and the second gripping member in the closed position, is pressed against the cauterizing element for sealing the blood vessel.

2. The device of claim 1 wherein the cauterizing element is further used to sever the blood vessel.

3. The device of claim 1 further comprising controls disposed near the proximal end of the elongated body for controlling the gripping members and for heating the cauterizing element.

4. The device of claim 1 wherein the tip has an inner cavity in communication with the one or more lumens and into which an endoscope is advanced for endoscopic viewing of a harvesting procedure performed by the device.

5. The device of claim 1 wherein the tip has sufficient axial strength to dissect a blood vessel to be sealed and cut from a surrounding tissue, while the tip is sufficiently deformable with the application of increased force.

6. The device of claim 1 wherein the first gripping member and the second gripping member are biased toward one another to secure the blood vessel therebetween.

7. The device of claim 1 wherein the first and second gripping members are individually translatable in the longitudinal direction substantially along a central axis of the cannula relative to the tip and distally past the tip, while maintaining the endoscopic view through the first and second gripping members.

8. The device of claim 1 wherein the first gripping member and the second gripping member are translatable as a unit relative to the tip and the unit is translatable distally past the tip.

9. The device of claim 1 wherein the cauterizing element is disposed on an inner face of the first gripping member or the second gripping member.

10. The device of claim 1 wherein the cauterizing element includes a first wire for transecting the blood vessel and a second wire for sealing the blood vessel, the second wire having a cross-section larger than a cross-section of the first wire.

11. A surgical device comprising:
    an elongated body extending between a proximal end and a distal end, and having one or more lumens extending through the elongated body;
    a deflectable tip disposed at the distal end of the elongated body;
    a gripping unit disposed about the deflectable tip, the gripping unit including a proximal member and a distal member configured to capture a blood vessel therebetween, the proximal and distal members being rings disposed concentrically around the deflectable tip, and the proximal and distal members being independently translatable in a longitudinal direction along the deflectable tip with respect to one another between an open position where the distal member is spaced away from the proximal member and a closed position where the distal member is next to the proximal member for gripping a blood vessel between the proximal member and the distal member; and
    a cauterizing element supported by the gripping unit so that the blood vessel captured by the gripping unit is pressed against the cauterizing element to allow the cauterizing element to seal the blood vessel.

12. The device of claim 11 wherein the cauterizing element is further used to sever the blood vessel.

13. The device of claim 11 wherein the deflectable tip has sufficient axial strength to dissect a blood vessel to be sealed and cut from a surrounding tissue, while the deflectable tip is sufficiently deformable with the application of increased force.

14. The device of claim 11 wherein the proximal member and the distal member are biased toward one another to secure the blood vessel therebetween.

15. The device of claim 11 wherein the proximal and distal members are individually translatable in the longitudinal direction substantially along a central axis of the cannula relative to the deflectable tip and distally past the deflectable tip, while maintaining the endoscopic view through the proximal and distal members.

16. The device of claim 11 wherein gripping unit is slidably disposed about the deflectable tip to enable axial movement of the gripping unit relative to the deflectable tip.

17. The device of claim 11 wherein the proximal member and the distal member are translatable together relative to the deflectable tip.

18. The device of claim 11 wherein the cauterizing element includes a first wire for severing the blood vessel and a second wire for cauterizing the blood vessel, the second wire having a cross-section larger than a cross-section of the first wire.

19. A method for harvesting a blood vessel comprising:
   inserting into an incision made to expose a main vessel a cannula having a dissection tip disposed at a distal tip of an elongated body and a gripping unit disposed concentrically around the dissection tip, the gripping unit comprising a ring shaped proximal member and a ring shaped distal member;
   advancing the dissection tip of the cannula along a main vessel to dissect the main vessel and its branch vessels from the surrounding tissue;
   activating the gripping unit to an open position where the proximal member and the distal member are spaced apart from one another in a longitudinal direction of the cannula;
   moving the gripping unit to a closed position where the proximal member and distal member are moved together to captured a branch vessel between the proximal member and the distal member;
   pressing the captured branch vessel against a cauterizing element supported by the gripping unit;
   energizing the cauterizing element to seal and sever the captured branch vessel.

20. The method of claim 19 further comprising:
   upon dissection of a desired length of the main vessel from the surrounding tissue and severing the branch vessels along the desired length of the main vessel, capturing the main vessel between the proximal member and the distal member;
   pressing the captured main vessel against the cauterizing element supported by the gripping unit; and
   energizing the cauterizing element to seal and sever the captured main vessel.

\* \* \* \* \*